United States Patent [19]

Palensky et al.

[11] Patent Number: 4,511,715
[45] Date of Patent: Apr. 16, 1985

[54] PLATINUM-NITROGEN COMPLEX CATALYSTS

[75] Inventors: Frederick J. Palensky, St. Paul; Allen R. Siedle, Lake Elmo, both of Minn.

[73] Assignee: Minnesota Mining and Manufacturing Company, St. Paul, Minn.

[21] Appl. No.: 402,231

[22] Filed: Jul. 27, 1982

Related U.S. Application Data

[63] Continuation-in-part of Ser. No. 245,927, Mar. 20, 1981, abandoned.

[51] Int. Cl.$^3$ .................. C07F 15/00; B01J 31/24; B01J 31/22
[52] U.S. Cl. .................. 544/225; 528/15; 544/179; 544/181; 548/102; 548/108; 548/101; 502/167
[58] Field of Search .................. 544/225, 181, 179; 548/101, 108, 102

[56] References Cited

U.S. PATENT DOCUMENTS

| | | | |
|---|---|---|---|
| 2,823,218 | 2/1958 | Speier | 260/448.2 |
| 3,159,601 | 12/1964 | Ashby | 260/46.5 |
| 3,178,464 | 4/1965 | Keith | 260/448.2 |
| 3,188,299 | 6/1965 | Chalk | 260/46.5 |
| 3,220,972 | 11/1965 | Lamoreaux | 260/46.5 |
| 3,419,593 | 12/1968 | Willing | 260/448.2 |
| 3,474,123 | 10/1969 | Kelly et al. | 260/448.2 |
| 3,516,946 | 6/1970 | Modic | 260/429 |
| 3,576,835 | 4/1971 | Smith | 544/225 |
| 3,652,615 | 3/1972 | Parasko | 544/225 |
| 3,715,334 | 2/1973 | Karstedt | 260/46.5 |
| 3,814,730 | 6/1974 | Karstedt | 260/46.5 |
| 3,879,416 | 4/1975 | Kraus | 548/101 |

FOREIGN PATENT DOCUMENTS 1165028 11/1962 Fed. Rep. of Germany.
2019462 10/1979 United Kingdom.

OTHER PUBLICATIONS

Doadrio et al., Chem. Abs. 94, 10880s.
Fraral et al., Chem. Abs. 87, 158d.
Stetsonke et al., Chem. Abs. 93, 230023j.
Singh et al., Chem. Abs. 83, 125467c.
Chottard et al., J. Amer. Chem. Soc. 99, 3531, (1977).
Bonivento, Chem. Abs. 94, 198169u.
Mulliez et al., Chem. Abs. 97, 182623p.

*Primary Examiner*—Mark L. Berch
*Attorney, Agent, or Firm*—Donald M. Sell; James A. Smith; Lorraine R. Sherman

[57] ABSTRACT

A hydrosilation process is disclosed for the reaction between silicon-hydrogen bonds and compounds having aliphatic carbon atoms linked by multiple bonds using as catalysts novel platinum-nitrogen complex compounds of the following classes:

(a) monometallic complexes, $(L)PtX_2(Y)$,
(b) bimetallic complexes, $(L)(PtX_2)_2(Y)_2$,
(c) ionic complexes, $(L)PtX_2(Y)(Z)$, and
(d) reduced forms of said monometallic complexes having the formulae:
  (1) $H[(PNZ)PtX_2(Q)]_2$,
  (2) $[(PNZ)PtX_2(Q)]_2^- A^+$, and
  (3) $[H(PNZ)PtCl_2(C_2H_4)]_3PtCl_3$ wherein L is a single or fused ring unsaturated heterocyclic ligand, wherein said hetero atoms are nitrogen, comprising at least one 5- or 6-member ring, said ligand having 2 to 4 nitrogen atoms in the same ring, and said ligand having up to a total of 44 carbon atoms, Y is an uncharged olefinically unsaturated hydrocarbon monodentate ligand that fills only one coordination position of the platinum atom and is selected from olefinically unsaturated hydrocarbons, triarylphosphines or triarylarsines wherein aryl is phenyl or phenyl substituted by up to 4 lower alkyl groups having 1 to 4 carbon atoms, dialkyl sulfides wherein each alkyl group independently has 1 to 16 carbon atoms, and carbon monoxide, the ligand having up to 25 carbon atoms, X is independently Cl, Br, I, CN, or SCN, Z is HCl, HBr, or silver trifluoromethanesulfonate, Q is an aliphatically unsaturated olefin ligand of 2 to 25 carbon atoms, A is a cation, and PNZ is phenazine.

Preparation of the novel catalysts is described. The cured compositions are useful in the preparation of molded articles.

22 Claims, No Drawings

PLATINUM-NITROGEN COMPLEX CATALYSTS

This is a continuation-in-part of copending application Ser. No. 245,927, filed Mar. 20, 1981, abn.

TECHNICAL FIELD

This invention relates to a novel class of platinum complex compounds and to their preparation. In another aspect, it relates to a process for hydrosilation using as catalysts platinum complex compounds. Compositions cured by hydrosilation reactions are useful in molding applications.

BACKGROUND ART

In the presence of catalysts, curable organosilicone compositions undergo hydrosilation, a reaction involving the addition of a silicon-hydrogen bond across a pair of aliphatic carbon atoms linked by multiple bonds. Reactions of this type are catalyzed by metals, most notably platinum (Pt), rhodium (Rh), iridium (Ir), and palladium (Pd), and compounds thereof. Hydrosilation has found widespread use in the production of silicone materials and organosilanes. Platinum-containing hydrosilation catalysts are known in the art and have been described in numerous patents, such as U.K. Patent Application GB No. 2,019,426 A, German Pat. No. 1,165,028, and U.S. Pat. Nos. 2,823,218, 3,814,730, 3,715,334, 3,516,946, 3,474,123, 3,419,593, 3,220,972, 3,188,299, 3,178,464, and 3,159,601. These catalysts often suffer from a number of disadvantages: they may be subject to "poisoning" in the presence of certain common materials; they may lack sufficient solubility or dispersibility in organic reaction media; they may be inefficient in promoting a reaction; and in their presence addition curable organosilicone compositions may lack stability and not exhibit satisfactory pot life.

U.S. Pat. No. 3,188,299 discloses nitrogen-containing compounds which are used with a platinum-containing catalyst to reduce or temporarily inhibit its activity in the presence of an alkenyl polysiloxane and a hydrogen polysiloxane. Although this patent discloses pyrazine as a useful ligand, the proportion of ligand to platinum catalyst used is considerably greater than Applicants' and thereby gives an entirely different product.

Other patents teaching hydrosilation nitrogen- and platinum-containing catalysts are U.K. Patent Application GB No. 2,019,426 A and German Pat. No. 1,165,028. The latter discloses trans-(pyridine)(ethylene).PtCl$_2$ as an effective hydrosilation catalyst. U.K. Patent Application GB No. 2,019,426 A teaches a process for the addition of a silicon-bonded hydrogen atom to an aliphatic multiple bond, which comprises carrying out the addition in the presence of a catalyst which comprises at least one halogen-platinum complex selected from those of the general formulae A$_2$PtX$_2$ and C$_3$H$_6$PtB$_2$X$_2$, in which formulae each A denotes a pyridine ring that is substituted by 1 or 2 alkyl radicals having 1 to 3 carbon atoms, and each X denotes a halogen atom, and each B denotes a 5- or 6-member unsubstituted or substituted heterocyclic ring having 1 to 2 hetero atoms or B$_2$ denotes two such rings joined together. Neither of these patents discloses a platinum catalyst that has the polynitrogen-containing single or fused ring structure which Applicants have discovered is important in providing increased stability and longer pot life to addition curable organosilicone compositions.

SUMMARY OF THE INVENTION

Briefly, in one aspect of the invention, there is provided a process for hydrosilation utilizing a platinum-nitrogen complex catalyst, said catalyst being a monometallic, bimetallic, or ionic complex, or reduced forms of the monometallic complex, said process comprising mixing an organosilicone composition, which can be an addition curable composition, with a catalytically effective amount of the platinum-nitrogen complex catalyst, optionally heating the resulting mixture to accelerate its reaction rate, and recovering the resulting organosilane or polysiloxane product.

"Monometallic" refers to a complex having only one platinum atom per molecule.

"Bimetallic" refers to a complex having two platinum atoms per molecule.

"Ionic" refers to a complex of a monometallic molecule and HCl, HBr, or the silver salt of trifluoromethanesulfonate, which complex dissociates to give positively and negatively charged moieties in certain solvents, e.g., nitromethane and acetonitrile.

"Reduced monometallic forms" refers to forms of monometallic complexes wherein an electron or a hydrogen atom is added to the nitrogen-containing ligand, to be discussed below in detail.

"Addition curing" refers to a hydrosilation reaction in which compounds having more than one pair of aliphatic carbon atoms linked by multiple bonds and compounds having more than one silicon-hydrogen bond react together to form a crosslinked polymer.

In another aspect of the invention there are provided novel hydrosilation catalysts.

The catalysts of this invention have increased stability, increased dispersibility in reaction media, give lower activation temperatures, are more active catalysts, provide compositions having longer pot life, and are less susceptible to poisoning, as compared to other platinum-containing hydrosilation catalysts.

"Pot life" is the time during which the composition containing the curable organosilicone components and the catalyst remains sufficiently fluid to be easily coatable, extrudable, or otherwise processed.

A further aspect of this invention relates to the method of preparing platinum-nitgrogen containing complex hydrosilation catalysts.

DETAILED DESCRIPTION

The hydrosilation catalysts of the present invention are of the following types or classes:
(a) monometallic complexes, (L)PtX$_2$(Y),
(b) bimetallic complexes, (L)(PtX$_2$)$_2$(Y)$_2$,
(c) ionic complexes, (L)PtX$_2$(Y)(Z), and
(d) reduced forms of said monometallic complexes having the formulae:
 (1) H[(PNZ)PtX$_2$(Q)]$_2$,
 (2) [(PNZ)PtX$_2$(Q)]$_2$$^-$A$^+$, and
 (3) [H(PNZ)PtCl$_2$(C$_2$H$_4$)]$_3$PtCl$_3$
wherein
L is a single or fused heterocyclic ligand comprising at least one 5- or 6-member ring, said ligand having 2 to 4 nitrogen ring atoms in the same ring,
Y is an uncharged monodentate ligand that fills only one coordination position of the platinum atom, such as olefins, alkyl- or aryl-substituted olefins, phosphines, arsines, sulfides, the ligands having up to 25 carbon atoms, X is independently Cl, Br, I, CN, or SCN, Z is HCl, HBr, or the silver salt of trifluoromethanesulfonate, Q is an aliphatically unsaturated olefin ligand of 2 to 25 carbon atoms, A is a cation, and PNZ is phenazine.

Y, an uncharged monodentate ligand, coordinates to the central platinum atom in the complex and occupies one coordination position. It is (a) an olefinically unsaturated hydrocarbon having the formula $R_2C=CR_2$, wherein each R is independently H, an alkyl group of up to 20 carbon atoms, or an aryl group having up to 10 ring carbon atoms, with the proviso that not more than two R groups are aryl, such as ethylene, propylene, butylene, and styrene; (b) a compound such as a triarylphosphine or triarylarsine wherein aryl is unsubstituted phenyl, such as triphenylphosphine or triphenylarsine, or phenyl substituted by up to 4 lower alkyl groups having 1 to 4 carbon atoms, such as tri-p-tolylphosphine or tri-p-tolylarsine; (c) CO: or (d) a dialkyl sulfide wherein each alkyl group independently has 1 to 16 carbon atoms, such as dimethyl sulfide, diethyl sulfide, and octyl ethyl sulfide.

The single or fused ring unsaturated (preferably aromatic) heterocyclic ligand, L, wherein the hetero atoms are nitrogen, has at least one nitrogen atom bonded to a platinum atom outside ligand L. Preferably ligand L is a cyclic structure containing two to four nitrogen ring atoms in the same ring, which structure can have one ring having five or six ring atoms, or two to six fused rings having up to 26 ring atoms. The nitrogen atoms in the same ring may be in any positions; they need not be para to each other. The single ring or fused rings are unsubstituted or some or all of the hydrogen atoms on the ring(s) may be substituted by phenyl or lower alkyl groups having 1 to 4 carbon atoms. L can have up to 44 carbon atoms. The two fused ring cyclic structure may be

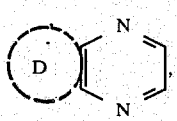
I wherein the encircled letter D denotes a 6-member carbocyclic aromatic or heterocyclic aromatic ring fused with the di-nitrogen heterocycle depicted in its simple (unsubstituted) form. Quinoxaline,

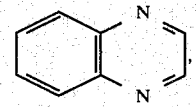

is the preferred species. In the three fused ring systems,

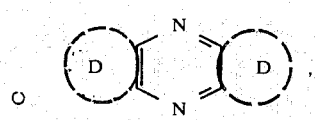
II wherein the encircled letters D each denote a 6-member carbocyclic aromatic or heterocyclic aromatic ring fused with the di-nitrogen heterocycle depicted in its simple (unsubstituted) form. Phenazine,

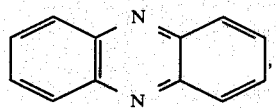

in this instance is the preferred species; phenazine oxide is also useful. Other useful ligands, of the single ring type, are imidazole, 1,2,4-triazole, pyrazine, and phenylpyrazine. Other useful ligands of the fused ring type are

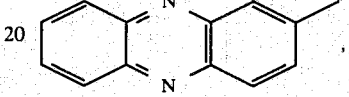

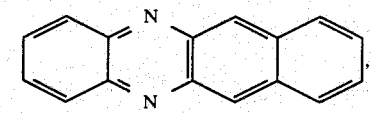

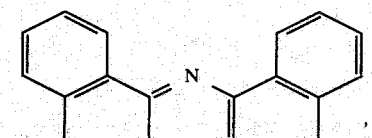

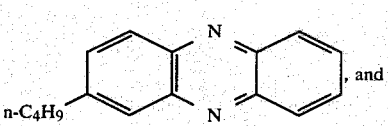, and

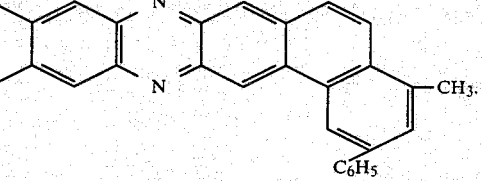

A is a solublizing cation such as a proton, an alkali metal ion such as Na+, K+, or Li+, an alkaline earth ion such as $\frac{1}{2}$Ca$^{+2}$ or $\frac{1}{2}$Mg$^{+2}$, a tetraalkylammonium or tetraalkylphosphonium or tetraalkylarsonium cation of the type R'$_4$N+, R'$_4$P+, or R'$_4$As+ wherein each R' independently is phenyl or an alkyl group having 1 to 16 carbon atoms, or A is bis(triphenylphosphine)iminium ion, i.e., [(C$_6$H$_5$)$_3$P]$_2$N+.

General preparative methods of the novel catalysts described above will now be described.

Monometallic catalysts of the type (L)PtX$_2$(Q), wherein L, X, and Q are as defined above, are prepared by combining a polynitrogen ligand L and KPtX$_3$(Q) in a 1:1 mole ratio in water or a polar organic solvent, such as methanol or acetonitrile. The latter is preferred. KPtX$_3$(Q) is prepared by methods known in the art (see A. Wold and J. Ruff, Ed., "Inorganic Synthesis", 14, 90, published 1973 by McGraw Hill) and the polynitrogen-containing single or fused ring substances (referred to herein as L) are commercially available. The complex salts precipitate from the reaction mixture. These olefin complexes may be subsequently converted to other novel catalytically active compositions by displacement of the olefin. For example, (L)PtX$_2$(Y) and (L)(PtX$_2$)$_2$(Y)$_2$, wherein L and X are as defined above and Y is a neutral ligand selected from diethyl sulfide, carbon monoxide, triphenylphosphine, triphenylarsine, and styrene, can be prepared by displacement of the olefin. Preferably the olefin, depicted as Q above, has the formula R$_2$C=CR$_2$, wherein each R is independently H, an alkyl group of up to 20 carbon atoms, or an aryl group having up to 10 ring carbon atoms, with the proviso that not more than two R groups are aryl. Typically, (L)PtX$_2$(Q) and the ligand Y are combined in a 1:1 molar ratio in an aprotic organic solvent such as benzene, chloroform, or acetonitrile and then heated at the reflux temperature. If CO is to be incorporated, it is used in excess because it is a gas. The (L)(PtX$_2$)(Y) compound is isolated by evaporation of the filtered reaction mixture.

Because Y contains more than 1 donor nitrogen atom, additional novel catalytically active bimetallic complexes of the formula (L)(PtX$_2$)$_2$(Y)$_2$ can be prepared in which at least two nitrogen atoms in the heterocyclic moiety are linked to platinum atoms. These complexes of the formula (L)(PtX$_2$)$_2$(Y)$_2$ are formed as coproducts with complexes of the formula (L)PtX$_2$(Y), wherein L, X and Y are as defined above, in the displacement reactions. They have low solubility in the reaction mixture and are easily isolated by filtration.

Ionic complex salts formed from complexes of the formula (L)PtX$_2$(Y) are prepared by combining the platinum compound and a protic acid (e.g., HBr or HCl) or a salt (e.g., AgCF$_3$SO$_3$) in a nonpolar organic solvent such as dichloromethane, benzene, or hexane, to yield complexes of the formula (L)PtX$_2$(Y)(Z) in which L, X, and Y are as defined above and Z is HBr, HCl, or AgCF$_3$SO$_3$.

Included also in the novel class of hydrosilation catalysts are the reduced forms of the monometallic complexes, wherein PNZ represents phenazine, and X and Q are as defined above. The reduction of the monometallic complexes of the invention leads to platinum complexes having enhanced reactivity and the reduction can be accomplished by electrolysis or by reaction with hydrogen, alkali metals, or silanes, as will be discussed below. These complexes and radicals have the formulae H[(PNZ)PtX$_2$(Q)]$_2$, [(PNZ)PtX$_2$(Q)]$_2$$^-$, and [H(PNZ)PtCl$_2$(C$_2$H$_4$)]$_3$PtCl$_3$, wherein PNZ, X, and Q are as defined above. By reduced form is meant addition of an electron or hydrogen atom to yield an oligomerized product of, for example, (phenazine)PtCl$_2$(ethylene). The dimeric H[(PNZ)PtCl$_2$(C$_2$H$_4$)]$_2$, so produced is useful as a hydrosilation catalyst and it is a more reactive catalyst than the precursor, (PNZ)PtCl$_2$(C$_2$H$_4$). Specifically, reduction of the monometallic phenazine platinum complexes to form H[(PNZ)PtX$_2$(Q)]$_2$ can be accomplished by using hydrogen in the presence of a platinum catalyst such as PtCl$_2$[(C$_2$H$_5$)$_2$S]$_2$ or, preferably, platinum black, in an aprotic solvent such as toluene or, preferably, dichloromethane, according to the following chemical equation:

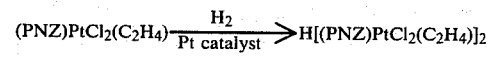

Reduction of (PNZ)PtX$_2$(Q) complexes is also accomplished by electrolysis in a polar organic solvent such as acetonitrile or dichloromethane and in the presence of a supporting electrolyte, such as tetra-n-butylammonium fluoroborate, until approximately 0.5 Faradays per mole of Pt have been consumed. Alternatively, reduction can be carried out using an alkali metal amalgam or an alkali metal with or without a carrier, such as naphthalene, being present. Solvents used in metal reductions are ethers, such as tetrahydrofuran or 1,2-dimethoxyethane. The molar ratio of alkali metal to platinum complex is 0.5 to 1 with further reduction leading to decomposition. For the (PNZ)PtCl$_2$(C$_2$H$_4$) complex, the three alternative reactions that take place are as follows:

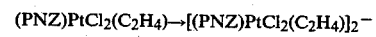

(1) electrolysis, or
(2) alkali metal amalgam, or
(3) alkali metal

Reduction of (PNZ)PtCl$_2$(C$_2$H$_4$) to form the catalyst [H(phenazine)PtCl$_2$(C$_2$H$_4$)]$_3$PtCl$_3$ occurs in chloroform. Suitable reductants include trialkyl-, triaryl- or trialkoxysilanes of the type R'$_{(4-n)}$SiH$_n$, wherein n is an integer of 1 to 3, R' is an alkyl group having up to 10 carbon atoms, an alkoxy group having up to 4 carbon atoms, phenyl, or diphenyl. Preferred silicon-containing reductants are (C$_6$H$_5$)$_3$SiH or (CH$_3$O)$_3$SiH. The reaction that takes place may be written as follows:

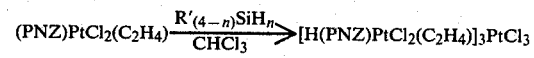

The proportion of complex present in the organosilicone compositions of the present invention can vary widely, but generally an amount sufficient to provide 1 to 1000 ppm by weight of platinum to the weight of the coreactants is useful.

The catalyst-containing organosilicone compositions of the present invention are formable materials ranging from thin pastes to stiff plastic, dough-like substances. They may be shaped, as by molding or extruding, after which the silicone article is converted to a rubbery state by curing. The rubbery fabricated articles formed thereby may be, for example, O-rings, gaskets, and tubing.

Objects and advantages of this invention are further illustrated by the following examples, but the particular materials and amounts thereof recited in these examples, as well as other conditions and details, should not be construed to unduly limit this invention.

EXAMPLE 1

Synthesis of the Complex Platinum-Nitrogen Catalysts

A. (Phenazine)PtCl$_2$(C$_2$H$_4$)

Phenazine, 3.3 mmole (0.60 g), in 20 ml hot acetonitrile was added to a solution of 3.3 mmole (1.28 g) KPtCl$_3$(C$_2$H$_4$) in 20 ml of the same solvent. The resulting turbid solution was allowed to stand at room temperature for 24 hours. The solids which separated were collected on a filter and recrystallized by slow evaporation of dichloromethane-ethanol solution to give 0.58 g of product as yellow needles. The original mother liquor was evaporated and the residue similarly recrystallized to give 0.32 g of additional product. The total yield was 0.90 g (59%). Spectroscopic analysis confirmed the product as (phenazine)$PtCl_2(C_2H_4)$. The infrared spectrum exhibited a single Pt-Cl stretching band indicative of trans stereochemistry. The analogous pyrazine and quinoxaline platinum-nitrogen complexes were prepared in a similar manner. Also, (phenazine)$PtCl_2(C_3H_6)$ can be prepared using $KPtCl_3(C_3H_6)$.

Using the same general method described above, the following complex catalysts were synthesized and their compositions were confirmed by elemental analysis.

TABLE I
Complex 1. (pyrazine)$PtCl_2(C_2H_4)$
2. (quinoxaline)$PtCl_2(C_2H_4)$
3. (phenazine)$PtCl_2P(C_6H_5)_3$
4. (phenazine)$PtCl_2(C_6H_5CH=CH_2)$
5. (phenazine-N-oxide)$PtCl_2(C_2H_4)$
6. (phenazine)$[PtCl_2(styrene)]_2$
7. $[2,3,5,6,-(CH_3)_4pyrazine]PtCl_2(C_2H_4)$
8. (phenazine)$PtCl_2(C_2H_4)\cdot AgCF_3SO_3$
9. (phenazine)$PtCl_2[S(C_2H_5)_2]$
10. (phenazine)$PtCl_2(C_2H_4)\cdot HCl$
11. (phenazine)$PtCl_2As(C_6H_5)_3$
12. (phenazine)$[PtCl_2As(C_6H_5)_3]_2$
13. (phenazine)$[PtCl_2P(C_6H_5)_3]_2$
14. (phenazine)$PtCl_2P(p-CH_3C_6H_4)_3$ B. (Phenazine)$PtCl_2(C_2H_4)\cdot CF_3SO_3Ag$ (Phenazine)$PtCl_2(C_2H_4)$, 1.0 mmole (0.47 g), in 30 ml hot benzene was added to a solution of 1.0 mmole (0.246 g) silver trifluoromethanesulfonate in 6 ml of the same solvent. After 15 minutes, the yellow product was collected on a filter, washed with benzene and vacuum dried. The yield was 0.57 g. Conductivity studies and spectroscopic analysis indicated the formation of (phenazine)$PtCl_2(C_2H_4)\cdot CF_3SO_3Ag$.

C. (Phenazine)$PtCl_2(C_2H_4)\cdot HCl$

A stream of anhydrous hydrogen chloride was passed through a solution of 0.5 g (phenazine)$PtCl_2(C_2H_4)$ in dichloromethane. The reaction mixture was filtered and the filtrate saved. The solids were recrystallized by slow evaporation of a dichloromethane-ethanol solution to give 0.1 g of product. The above filtrate was treated with heptane and concentrated to give solids which were similarly recrystallized to give 0.15 g additional products. Spectroscopic and elemental analyses were the same for the two crops and confirmed the identity of the compound to be compound 10 in Table I.

D. (Heterocyclic amine)$PtCl_2(CO)$ complexes

Approximately 0.05 g quantities of (amine)$PtCl_2(C_2H_4)$, where the amines are listed below in Table II, were placed in vials which were sealed with rubber septa. The vials were thoroughly flushed with nitrogen, then about 1 ml deoxygenated dichloromethane was introduced via syringe. Carbon monoxide was slowly passed through the solutions to effect olefin displacement and formation of the carbonyl complex; this was usually accompanied by a decrease in the intensity of the yellow color. Samples were withdrawn by syringe and spectroscopic analysis showed the presence of the corresponding (heterocyclic amine)$PtCl_2(CO)$; e.g., where pyrazine was used the resulting complex was (pyrazine)$PtCl_2(CO)$.

TABLE II pyrazine
quinoxaline
phenazine
phenazine-N-oxide
2,6-dimethylpyrazine
2,3,5,6-tetramethylpyrazine E. (Phenazine)$PtCl_2P(C_6H_5)_3$ and (phenazine)$[PtCl_2P(C_6H_5)_3]_2$ Triphenylphosphine (0.5 mmole, 0.13 g) and 0.24 g (0.5 mmole) (phenazine)$PtCl_2(C_2H_4)$ in 10 ml acetonitrile were refluxed and stirred overnight. The bimetallic catalyst (phenazine)$[PtCl_2P(C_6H_5)_3]_2$ precipitated from the hot reaction mixture and was isolated by filtration. The yield was 0.1 g. The monometallic catalyst (PNZ)$PtCl_2P(C_6H_5)_3$ remained dissolved in the filtrate which was concentrated and cooled to give upon recrystallization from acetonitrile 0.18 g of (PNZ)$PtCl_2P(C_6H_5)_3$ as yellow plates. Spectroscopic analysis confirmed the indentity of the products.

The styrene and triphenylarsine analogues were prepared in a similar manner. Spectroscopic analysis (see compounds 4, 6, 11, and 12 of Table I above) confirmed the identity of these products.

F. (Imidazole)$PtCl_2(C_2H_4)$ and (1,2,4-triazole)$PtCl_2(C_2H_4)$

To a solution of 0.37 g (1 mmole) $KPtCl_3(C_2H_4)$ in 15 ml water was added with stirring 0.068 g (1 mmole) imidazole, dissolved in 3 ml water. The desired (imidazole)$PtCl_2(C_2H_4)$ separated as a yellow microcrystalline solid and was collected on a filter, washed with water and vacuum dried. The yield was 0.26 g, m.p. 119°-120°. Elemental analysis confirmed the product to be (imidazole)$PtCl_2(C_2H_4)$. (Imidazole)$PtCl_2(C_3H_6)$ can be prepared from $KPtCl_3(C_3H_6)$ using this method.

A similar synthesis of (1,2,4-triazole)$PtCl_2(C_2H_4)$ using 1,2,4-triazole was carried out. The yield was 0.18 g (50%). This compound did not melt and underwent only slight darkening on heating to 320° C. Elemental analysis confirmed the product to be (1,2,4-triazole)$PtCl_2(C_2H_4)$.

EXAMPLE 2

Reduction of Complex Platinum-Nitrogen Catalysts

A. Reduction of (phenazine)$PtCl_2(C_2H_4)$ with hydrogen

A solution of 0.40 g of (phenazine)$PtCl_2(C_2H_4)$ in 20 ml dichloromethane was prepared under nitrogen. Platinum black (5 mg) was added and a slow stream of hydrogen passed over the stirred reaction mixture for 3.5 hours. Filtration afforded 0.26 g of product as a dark green solid which was washed with dichloromethane, dried by pumping and stored under vacuum. Spectroscopic and elemental analyses confirmed the identity of the product to be $H[(phenazine)PtCl_2(C_2H_4)]_2$.

B. Electrochemical reduction of (phenazine)$PtCl_2(C_2H_4)$

Electrochemical measurements in this example were made using the conventional three electrode technique. A water jacketed cell maintained at 4° C. held the sample which was dissolved in 0.1M tetrabutylammonium fluoroborate in dichloromethane. Nitrogen presaturated with solvent was used to deoxygenate the solutions.

Reduction of (phenazine)$PtCl_2(C_2H_4)$ was carried out at −0.9 V (relative to a saturated calomel reference electrode) until the current had declined to 4% of the initial value at which point 0.49 Faradays per mole of platinum had been passed. Aliquots of the deep green solution were transferred with a syringe to lnitrogen filled EPR tubes or to a rectangular cuvette for electronic spectroscopy. Spectroscopic analysis confirmed the identity of [(phenazine)PtCl$_2$(C$_2$H$_4$)]$_2^-$. The cation A was the tetrabutylammonium ion from the supporting electrolyte. Similarly, a tetraphenylarsonium salt, a trimethyldecylammonium salt, and a methyltriphenylphosphonium salt can be prepared using the appropriate supporting electrolyte in place of tetrabutylammonium fluoroborate.

C. Reduction of (phenazine)PtCl$_2$(C$_2$H$_4$) with sodium metal

Five milliliters of degassed acetonitrile (dried with 5A molecular sieves) were condensed onto 0.047 g (phenazine)PtCl$_2$(C$_2$H$_4$) and 0.26 g of 0.44% sodium amalgam. After shaking for about five minutes, the green solution was filtered through a coarse frit into an EPR tube. A sample for electronic spectroscopy was similarly prepared. The epr and visible spectrum confirmed the identity of [(PNZ)PtCl$_2$(C$_2$H$_4$)]$_2^-$. The product matched that of the material prepared electrochemically, in EXAMPLE 2B, except that the cation was sodium ion.

Similar reductions were carried out using sodium amalgam in dimethoxyethane or sodium naphthalide in tetrahydrofuran with similar results. When these reactions were carried out for a prolonged period, the green color was replaced by the red phenazine anion radical and eventually a platinum mirror formed on the walls of the reaction vessel.

EXAMPLE 3

Reaction of (phenazine)PtCl$_2$(C$_2$H$_4$) with Triphenylsilane

A mixture of 0.47 g of the platinum compound, 0.27 g triphenylsilane, and 25 ml. chloroform (freshly distilled from CaSO$_4$) was stirred under nitrogen for 15 min. then allowed to stand for 3 hr. The fine black microcrystals, 0.23 g, were collected on a frit, washed with fresh solvent, vacuum dried and stored under nitrogen. Spectroscopic and elemental analyses confirmed the identity of [H(PNZ)PtCl$_2$(C$_2$H$_4$)]$_3$PtCl$_3$.

Other silanes found capable of reducing (PNZ)PtCl$_2$(C$_2$H$_4$) were 1,1,2-trimelthyldisilane, 1,1,1-trimethyldisilane, diethoxysilane, phenylsilane, diethylsilane, octylsilane, pentamethyldisiloxane, and diphenylsilane.

EXAMPLE 4

Hydrosilation Reactions

A. Hydrosilation of 1-methylcyclohexene using a Pt-N complex catalyst

A mixture of 20 ml trichlorosilane, 25 ml chloroform, 8.1 g 1-methylcyclohexene and 0.055 g (phenazine)PtCl$_2$(C$_2$H$_4$) was refluxed and stirred under nitrogen for 6 days. Distillation of the reaction mixture afforded 2.2 g of trichlorosilylmethylcyclohexane C$_6$H$_{11}$CH$_2$SiCl$_3$ which was characterized by its mass and NMR spectra.

B. Addition Curing by Hydrosilation

At the concentration shown below in Table III, several platinum catalysts were dispersed in an oligomer fluid of average composition A.

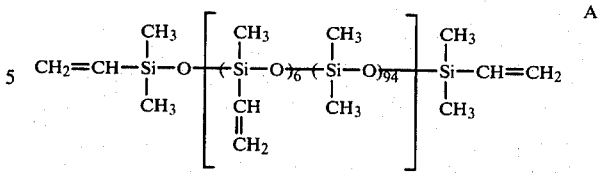

A crosslinking agent of oligomer composition B

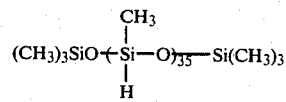

was added at 5 wt% of the total composition. The temperature at which gelatin (formation of a rigid polymer) occurred in less than 5 sec. (i.e., the activation temperature) was determined on a "Kofler Heizbank" hot bar (Reichert, Austria). Hydrosilation caused crosslinking of the oligomers with a drastic increase in viscosity; a very active catalyst yielded a rigid polymer in all cases. The results are shown below in Table III and indicate that (phenazine)PtCl$_2$(C$_2$H$_4$) provides lower activation temperatures and longer gel times at ambient temperatures than the controls, complex catalysts (pyridine)PtCl$_2$(C$_2$H$_4$) and PtCl$_2$[S(C$_2$H$_5$)$_2$]$_2$. This is particularly apparent in the cases where the catalysts are used at low concentrations. Low concentrations of platinum are desirable due to the high cost of this chemical element.

TABLE III

| Catalyst | Pt conc., ppm* | Activation temp.,** °C. | Gel time,*** hours @ 27° C. |
|---|---|---|---|
| (phenazine)PtCl$_2$(C$_2$H$_4$) | 100 | 100 | 0.5 |
|  | 50 | 110 | 3 |
|  | 10 | 120 | 10 |
| (pyridine)PtCl$_2$(C$_2$H$_4$) (control) | 100 | 110 | 0.2 |
|  | 50 | 130 | 3 |
|  | 10 | 150 | 4 |
| PtCl$_2$[S(C$_2$H$_5$)$_2$]$_2$ (control) | 100 | 110 | 0.1 |
|  | 50 | 120 | 0.5 |
|  | 10 | 130 | 2 |

*relative to weight of A
**temperature at which gelation occurs in <5 sec
***time required to form a rigid polymer at 27° C. using ASTM method D-2471-71, reapproved 1979

The above data also show that (phenazine)PtCl$_2$(C$_2$H$_4$) oligomer mixture was more stable in that it had a pot life 2½ times longer than that of the controls but had an activation temperature 30° C. lower than (pyridine)PtCl$_2$(C$_2$H$_4$) at 10 ppm Pt concentration. Lower activation temperature is particularly advantageous when it is desired to carry out the curing process on a thermally labile substrate.

Using the same general method just described, the following complexes were found to exhibit similar catalytic activity in the curing of oligomers A and B:

TABLE IV

Complex (phenazine)PtCl$_2$(C$_2$H$_4$).AgSO$_3$CF$_3$
(phenazine)PtCl$_2$(styrene)
(phenazine)PtCl$_2$(C$_2$H$_4$).HCl
(phenazine)PtCl$_2$S(C$_2$H$_5$)$_2$
(quinoxaline)PtCl$_2$(C$_2$H$_4$)

(pyrazine)PtCl$_2$(C$_2$H$_4$)
(phenazine)PtCl$_2$P(C$_6$H$_5$)$_3$
(phenazine oxide)PtCl$_2$(C$_2$H$_4$)
H[(phenazine)PtCl$_2$(C$_2$H$_4$)]$_2$
[(C$_4$H$_9$)$_4$N][(phenazine)PtCl$_2$(C$_2$H$_4$)]$_2$
[H(phenazine)PtCl$_2$(C$_2$H$_4$)]$_3$PtCl$_3$ H[(phenazine)PtCl$_2$(C$_2$H$_4$)]$_2$ and H$_3$[(phenazine)PtCl$_3$(C$_2$H$_4$)]$_3$, prepared in Example 3, were also found to have activity (at 100 ppm Pt) as hydrosilation catalysts. A concentration of 100 ppm Pt of the complex to be tested was added to oligomers A and B and the mixture stirred. Hydrosilation caused crosslinking of the oligomers with a drastic increase in viscosity.

C. Shaped Article

The polymer produced in B. above, using (phenazine)PtCl$_2$(ethylene) as the catalyst, was poured into a heated mold (110° C.) shaped as a gasket. A solid, rubbery gasket was extracted from the mold after 15 min.

Various modifications and alterations of this invention will become apparent to those skilled in the art without departing from the scope and spirit of this invention, and it should be understood that this invention is not to be unduly limited to the illustrative embodiments set forth herein.

We claim:

1. A platinum-nitrogen complex compound selected from classes of complexes having the formulae:
(a) monometallic complexes, (L)PtX$_2$(Y),
(b) bimetallic complexes, (L)(PtX$_2$)$_2$(Y)$_2$,
(c) ionic complexes, (L)PtX$_2$(Y)(Z), and
(d) reduced forms of said monometallic complexes having the formulae:
 (1) H[(PNZ)PtX$_2$(Q)]$_2$,
 (2) [(PNZ)PtX$_2$(Q)]$_2^-$A$^+$, and
 (3) [H(PNZ)PtCl$_2$(C$_2$H$_4$)]$_3$PtCl$_3$
wherein L is a single ring or fused 2- to 6-ring unsaturated heterocyclic ligand wherein said hereto atoms are nitrogen, said ligand having only 2 to 4 nitrogen atoms in exactly one 6-membered ring, at least one of which nitrogen atoms is bonded to a platinum atom, ligand L being selected from 5- and 6-member rings, and said ligand having up to a total of 26 ring atoms and can be unsubstituted or substituted by phenyl or lower alkyl groups for a total of up to 44 carbon atoms, Y is a monodentate ligand that fills only one coordination position of the platinum atom and is selected from (1) olefinically unsaturated hydrocarbons, (2) triarylphosphines or triarylarsines wherein aryl is phenyl or phenyl substituted by up to 4 ower alkyl groups having 1 to 4 carbon atoms, (3) dialkyl sulfides wherein each alkyl group independently has 1 to 16 carbon atoms, and (4) carbon monoxide, the ligand having up to 25 carbon atoms, X is independently Cl, Br, I, Cn, or SCN, Z is HCl, HBr, or silver trifluoromethanesulfonate, Q is an olefinically unsaturated hydrocarbon ligand of 2 to 25 carbon atoms, A is a solubilizing cation, and PNZ is phenazine.

2. The platinum-nitrogen complex compound according to claim 1 wherein Y represents an olefin ligand having the formula R$_2$C=CR$_2$, wherein each R is independently H, an alkyl group of up to 20 carbon atoms, or an aryl group having up to 10 ring carbon atoms, with the proviso that not more than two R groups are aryl.

3. The platinum-nitrogen complex compound according to claim 2 wherein Y is selected from ethylene, propylene, butylene, or styrene.

4. The platinum-nitrogen complex compound according to claim 1 wherein Y is selected from triphenylphosphine, tri-p-tolylphosphine, triphenylarsine, tri-p-tolylarsine, (CH$_3$)$_2$S, and (C$_2$H$_5$)$_2$S.

5. The platinum-nitrogen complex compound according to claim 1 wherein L represents a cyclic dinitrogen compound.

6. The platinum-nitrogen complex compound according to claim 1 wherein L represents a quinoxaline compound.

7. The platinum-nitrogen complex compound according to claim 1 wherein L represents a phenazine compound.

8. The platinum-nitrogen complex compound according to claim 1 wherein Q represents an olefin ligand having the formula R$_2$C=CR$_2$, wherein each R is independently H, an alkyl group of up to 20 carbon atoms, or an aryl group having up to 10 ring carbon atoms, with the proviso that not more than two R groups are aryl.

9. The platinum-nitrogen complex compound according to claim 1 wherein A is a cation selected from a proton, an alkali metal ion, an alkaline earth metal ion, a tetraalkylammonium, tetraalkylphosphonium, or tetraalkylarsonium ion, or a bis(triphenylphosphine)iminium ion.

10. The platinum-nitrogen complex compound according to claim 1 wherein the reduced form of the catalyst is H[phenazine)PtCl$_2$(ethylene)].

11. The platinum-nitrogen complex compound (phenezine)PtCl$_2$(C$_2$H$_4$) according to claim 1.

12. A platinum-nitrogen complex compound selected from classes of complexes having the formulae:
(a) monometallic complexes, (L)PtX$_2$(Y),
(b) bimetallic complexes, (L)(PtX$_2$)$_2$(Y)$_2$,
(c) ionic complexes, (L)PtX$_2$(Y)(Z), and
(d) reduced forms of said monometallic complexes having the formulae:
 (1) H[l(PNZ)PtX$_2$(Q)]$_2$,
 (2) [(PNZ)PtX$_2$(Q)]$_2^-$A$^+$, and
 (3) [H(PNZ)PtCl$_2$(C$_2$H$_4$)]$_3$PtCl$_3$
wherein L is a single ring or fused 2- to 6-ring unsaturated heterocyclic ligand wherein said hetero atoms are nitrogen, said ligand having only 2 nitrogen atoms in exactly one 6-member ring, at least one of which nitrogen atoms is bonded to a platinum atom, ligand L being selected from 6-member rings, and said ligand having up to a total of 26 ring atoms and can be unsubstituted or substituted by phenyl or lower alkyl groups for a total of up to 44 carbon atoms, Y is a monodentate ligand that fills only one coordination position of the platinum atom and is selected from (1) olefinically unsaturated hydrocarbons, (2) triarylphosphines or triarylarsines wherein aryl is phenyl or phenyl substituted by up to 4 lower alkyl groups having 1 to 4 carbon atoms, (3) dialkyl sulfides wherein each alkyl group independently has 1 to 16 carbon atoms, and (4) carbon monoxide, the ligand having up to 25 carbon atoms, X is independently Cl, Br, I, CN, or SCN, Z is HCl, HBr, or silver trifluoromethanesulfonate,
Q is an olefinically unsaturated hydrocarbon ligand of 2 to 25 carbon atoms,
A is a solubilizing cation, and
PNZ is phenazine.

13. The platinum-nitrogn complex compound (phenazine)PtCl$_2$(C$_3$H$_6$) according to claim 1.

14. The platinum-nitrogen complex compound according to claim 12 wherein Y is selected from ethylene, propylene, butylene, and styrene.

15. The platinum-nitrogen complex compound (pyrazine)PtCl$_2$(C$_2$H$_4$) according to claim 1.

16. The platinum-nitrogen complex compound [2,3,5,6-(CH$_3$)$_4$pyrazine]PtCl$_2$(C$_2$H$_4$) according to claim 1.

17. The platinum-nitrogen complex compound according to claim 12 wherein L represents a quinoxaline compound.

18. The platinum-nitrogen complex compound according to claim 12 wherein L represents a phenazine compound.

19. The platinum-nitrogen complex compound according to claim 18 wherein said compound is selected from (phenazine)PtCl$_2$(C$_2$H$_4$) and (phenazine)PtCl$_2$(C$_3$H$_6$).

20. A platinum-nitrogen complex compound wherein said compound is (phenazine-N-oxide)PtCl$_2$(C$_2$H$_4$).

21. A platinum-nitrogen complex compound selected from classes of complexes having the formulae:
(a) monometallic complexes, (L)PtX$_2$(Y),
(b) bimetallic complexes, (L)(PtX$_2$)$_2$(Y)$_2$,
(c) ionic complexes, (L)PtX$_2$(Y)(Z), and
(d) reduced forms of said monometallic complexes having the formulae:
  (1) H[(PNZ)PtX$_2$(Q)]$_2$,
  (2) [(PNZ)PtX$_2$(Q)]$_2^-$A$^+$, and
  (3) [H(PNZ)PtCl$_2$(C$_2$H$_4$)]$_3$PtCl$_3$
wherein
L is a single ring or fused 2- to 6-ring unsaturated heterocyclic ligand wherein said hetero atoms are nitrogen, said ligand having only 3 nitrogen atoms in exactly one 5-member ring, at least one of which nitrogen atoms is bonded to a platinum atom, ligand L being selected from 5- and 6-member rings, and said ligand having up to a total of 26 ring atoms and can be unsubstituted or substituted by phenyl or lower alkyl groups for a total of up to 44 carbon atoms,
Y is a mondentate ligand that fills only one coordination position of the platinum atom and is selected from (1) olefinically unsaturated hydrocarbons, (2) triarylphosphines or triarylarsines wherein aryl is phenyl or phenyl substituted by up to 4 lower alkyl groups having 1 to 4 carbon atoms, (3) dialkyl sulfides wherein each alkyl group independently has 1 to 16 carbon atoms, and (4) carbon monoxide, the ligand having up to 25 carbon atoms,
X is independently Cl, Br, I, CN, or SCN,
Z is HCl, HBr, or silver trifluoromethanesulfonate,
Q is an olefinically unsaturated hydrocarbon ligand of 2 to 25 carbon atoms,
A is a solubilizing cation, and
PNZ is phenazine.

22. A platinum-nitrogen complex compound selected from classes of complexes having the formulae:
(a) monometallic complexes, (L)PtX$_2$(Y),
(b) bimetallic complexes, (L)(PtX$_2$)$_2$(Y)$_2$,
(c) ionic complexes, (L)PtX$_2$(Y)(Z), and
(d) reduced forms of said monometallic complexes having the formulae:
  (1) H[(PNZ)PtX$_2$(Q)]$_2$,
  (2) [(PNZ)PtX$_2$(Q)]$_2^-$A$^+$, and
  (3) [H(PNZ)PtCl$_2$(C$_2$H$_4$)]$_3$PtCl$_3$
wherein
L is a single ring or fused 2- to 6-ring unsaturated heterocyclic ligand wherein said hetero atoms are nitrogen, said ligand having only 4 nitrogen atoms in exactly one 5-membered ring, at least one of which nitrogen atoms is bonded to a platinum atom, ligand L being selected from 5- and 6-member rings, and said ligand having up to a total of 26 ring atoms and can be unsubstituted or substituted by phenyl or lower alkyl groups for a total of up to 44 carbon atoms,
Y is a monodentate ligand that fills only one coordination position of the platinum atom and is selected from (1) olefinically unsaturated hydrocarbons, (2) triarylphosphines or triarylarsines wherein aryl is phenyl or phenyl substituted by up to 4 lower alkyl groups having 1 to 4 carbon atoms, (3) dialkyl sulfides wherein each alkyl group independently has 1 to 16 carbon atoms, and (4) carbon monoxide, the ligand having up to 25 carbon atoms,
X is independently Cl, Br, I, Cn, or SCN,
Z is HCl, HBr, or silver trifluoromethanesulfonate,
Q is an olefinically unsaturated hydrocarbon ligand of 2 to 25 carbon atoms,
A is a solubilizing cation, and
PNZ is phenazine.

* * * * *